United States Patent [19]
Houser et al.

[11] Patent Number: 5,833,604
[45] Date of Patent: Nov. 10, 1998

[54] VARIABLE STIFFNESS ELECTROPHYSIOLOGY CATHETER

[75] Inventors: Russell A. Houser, Livermore; Tom Bourne, Mountain View, both of Calif.

[73] Assignee: E.P. Technologies, Inc., San Jose, Calif.

[21] Appl. No.: 738,825

[22] Filed: Oct. 28, 1996

Related U.S. Application Data

[63] Continuation of Ser. No. 420,448, Apr. 10, 1995, abandoned, which is a continuation of Ser. No. 100,739, Jul. 30, 1993, abandoned.

[51] Int. Cl.⁶ ..................................................... A61B 5/04
[52] U.S. Cl. ........................... 600/373; 607/122; 604/280
[58] Field of Search ..................................... 128/642, 639, 128/772, 657; 604/280, 282, 264, 95; 607/116, 119, 122; 600/373, 372, 585, 434

[56] References Cited

U.S. PATENT DOCUMENTS

| | | | |
|---|---|---|---|
| 3,605,725 | 9/1971 | Bentov . | |
| 4,245,624 | 1/1981 | Komiya | 128/772 |
| 4,273,111 | 6/1981 | Tsukaya | 128/772 X |
| 4,586,923 | 5/1986 | Gould et al. | 128/657 X |
| 4,676,249 | 6/1987 | Arenas et al. | 128/657 |
| 4,677,990 | 7/1987 | Neubauer | 607/119 |
| 4,873,983 | 10/1989 | Winters . | |
| 4,886,067 | 12/1989 | Palermo | 128/772 X |
| 4,909,787 | 3/1990 | Danforth . | |
| 4,917,102 | 4/1990 | Miller et al. . | |
| 4,920,980 | 5/1990 | Jackowski | 128/642 X |
| 5,010,894 | 4/1991 | Edhag . | |
| 5,040,543 | 8/1991 | Badera et al. . | |
| 5,055,101 | 10/1991 | McCoy | 128/772 X |
| 5,083,565 | 1/1992 | Parins . | |
| 5,108,368 | 4/1992 | Hammerslag et al. | 128/772 X |
| 5,170,787 | 12/1992 | Lindegren | 128/772 X |
| 5,190,050 | 3/1993 | Nitzsche | 128/772 |
| 5,203,772 | 4/1993 | Hammerslag et al. . | |
| 5,228,441 | 7/1993 | Lundquist | 128/642 |
| 5,231,989 | 8/1993 | Middleman et al. | 128/772 X |
| 5,254,088 | 10/1993 | Lundquist et al. | 128/772 X |
| 5,255,668 | 10/1993 | Umeda | 128/772 X |
| 5,273,535 | 12/1993 | Edwards et al. . | |
| 5,275,151 | 1/1994 | Shockey et al. | 128/772 X |
| 5,306,245 | 4/1994 | Heaven | 604/280 X |
| 5,330,466 | 7/1994 | Imran | 604/280 X |
| 5,364,352 | 11/1994 | Cimino et al. | 604/280 |
| 5,389,072 | 2/1995 | Imran | 604/95 |
| 5,389,073 | 2/1995 | Imran | 604/95 |
| 5,391,147 | 2/1995 | Imran et al. | 128/657 |
| 5,487,757 | 1/1996 | Truckai et al. | 607/119 |

FOREIGN PATENT DOCUMENTS 0 600 676  6/1994  European Pat. Off. .

*Primary Examiner*—Brian L. Casler
*Attorney, Agent, or Firm*—Oppenheimer Wolff & Donnelly LLP

[57] ABSTRACT

A catheter supporting a tip electrode for percutaneous insertion into a living body having a steering mechanism that includes an elongated body bendable in response to external forces to steer the tip electrode. An axially movable stiffening member, preferably in the form of a sleeve or rod provides a variable resistance to bending of the body in response to an applied bending force. A control stylet or sleeve extends through the catheter and is attached to the stiffening member for moving the stiffening member in a distal/proximal direction relative to the body.

11 Claims, 3 Drawing Sheets

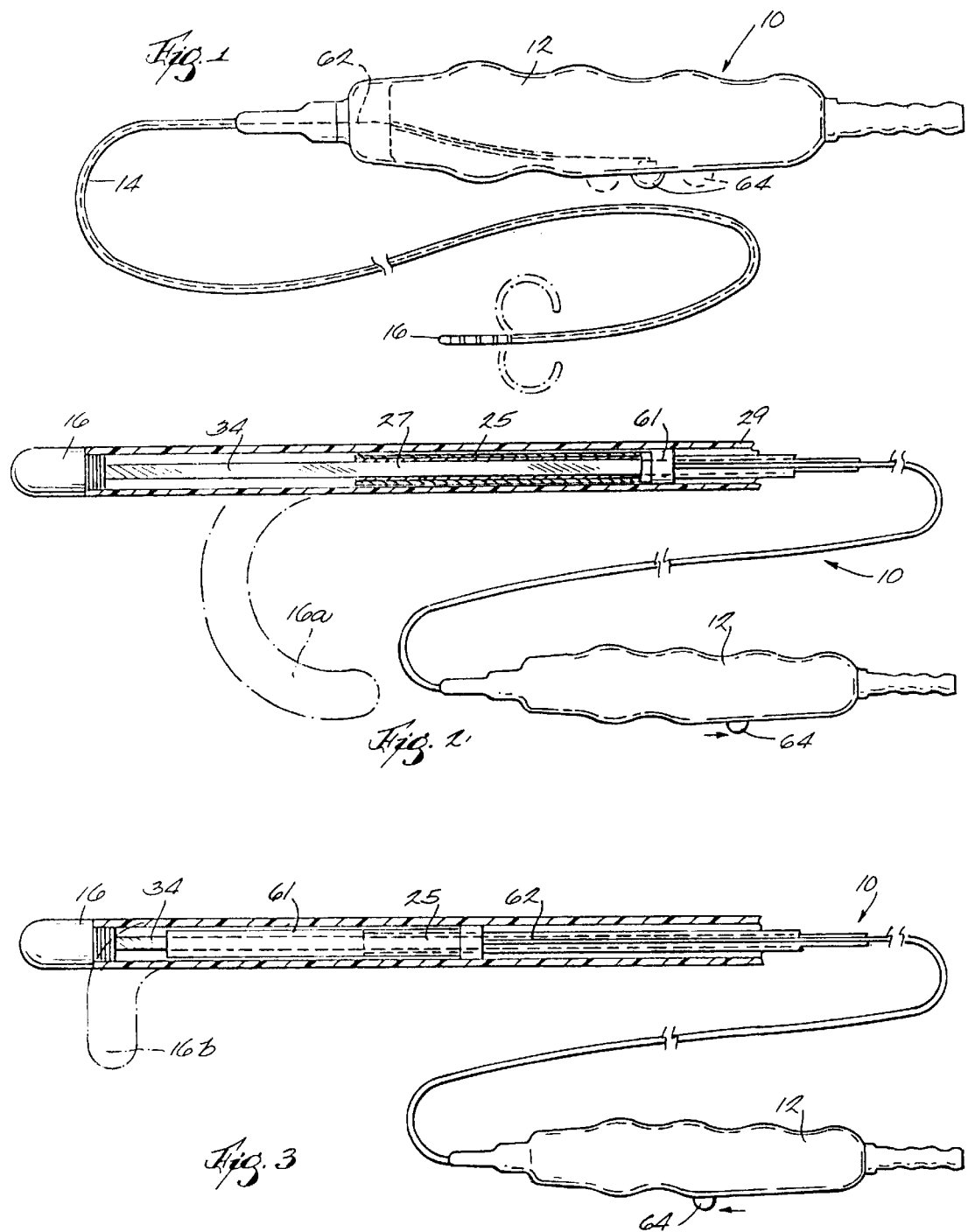

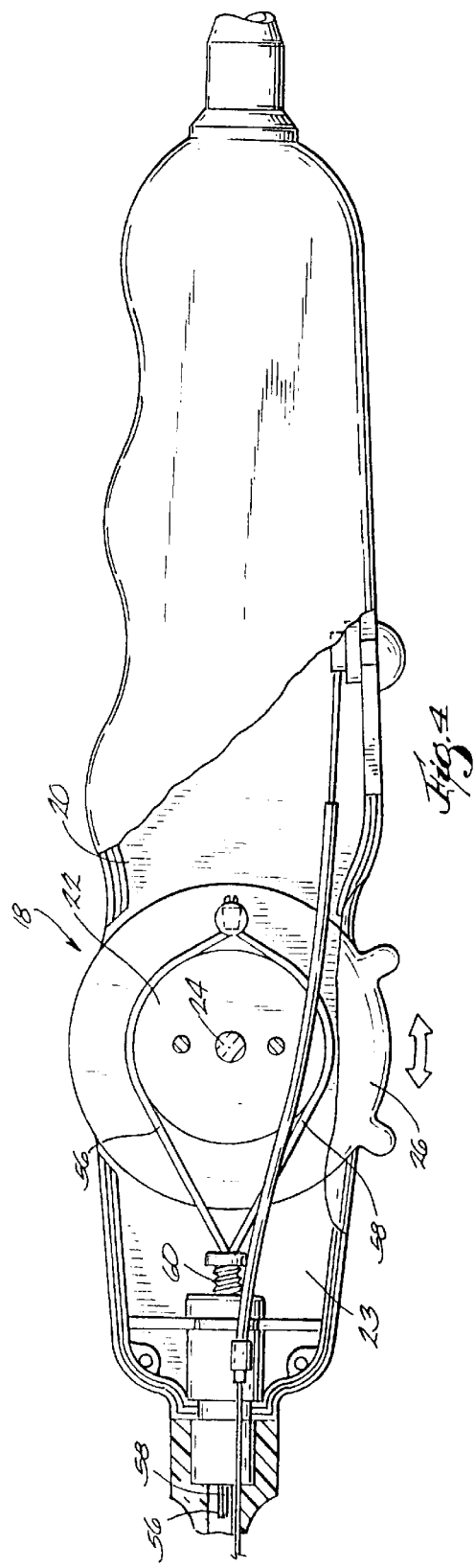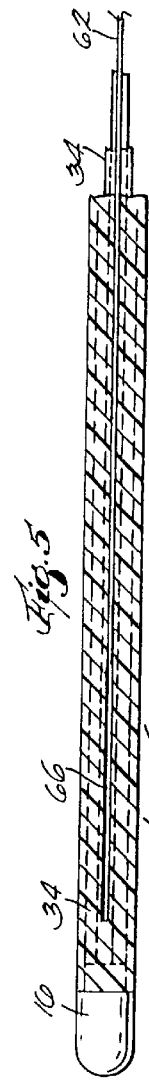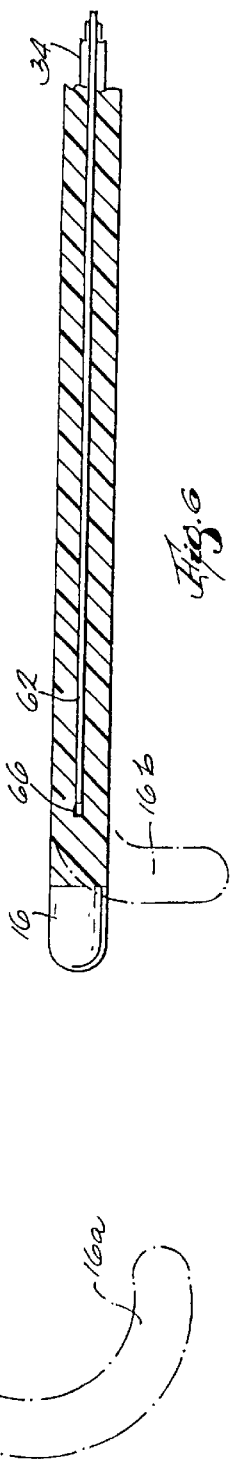

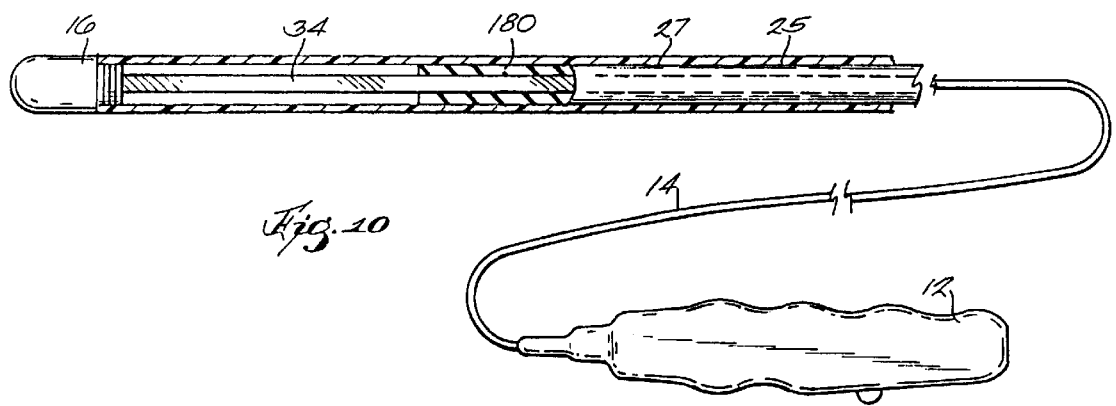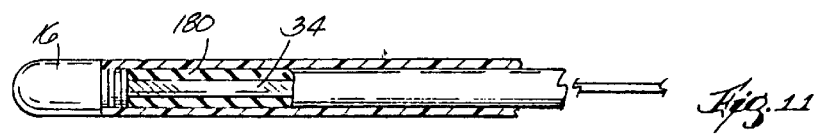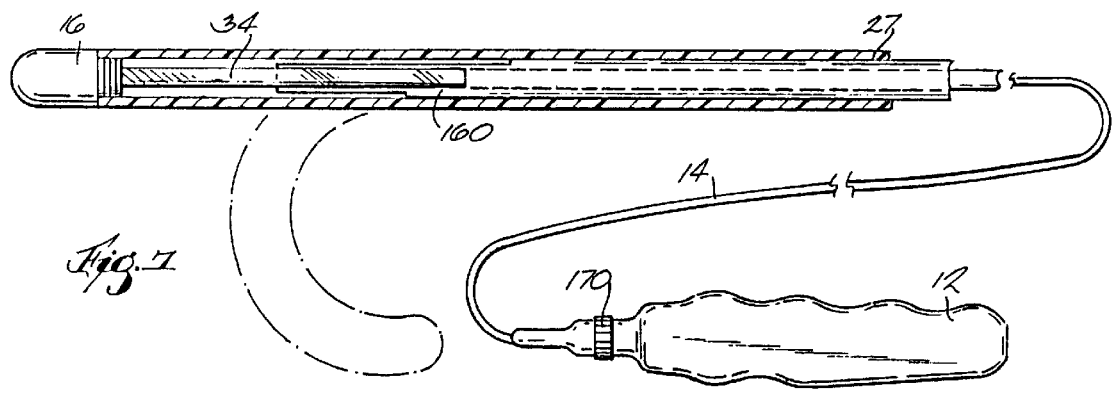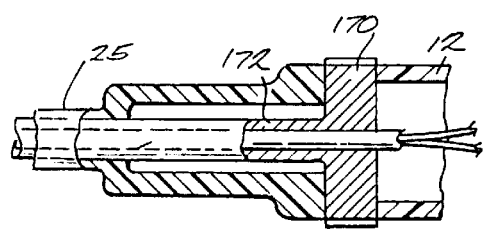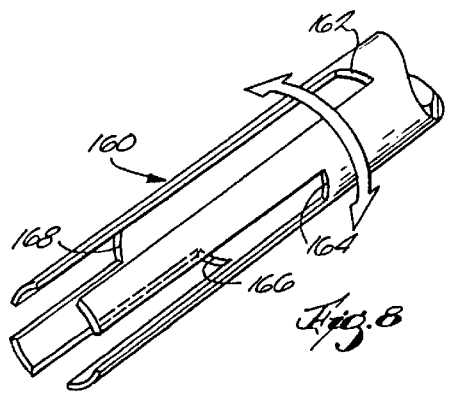

VARIABLE STIFFNESS ELECTROPHYSIOLOGY CATHETER

This is a continuation of application Ser. No. 08/420,448 filed on Apr. 10, 1995 now abandoned, which is a continuation of application Ser. No. 08/100,739 filed Jul. 30, 1993 (abandoned).

FIELD OF THE INVENTION

This invention relates to catheters that can by steered by external controls.

BACKGROUND OF THE INVENTION

Cardiac mapping is used to locate aberrant electrical pathways and currents emanating within the heart. Such aberrant pathways cause irregular contractions of the heart muscle resulting in life-threatening patterns or disrhythmias.

Intercardiac mapping requires careful positioning of the electrodes within the heart. Various steering mechanisms for catheters carrying such electrodes have heretofore been developed and used.

To provide catheters having different stiffness characteristics to access various endocardial sites, physicians have to stock and use number of different catheters, each of which provides a different characteristic. The use of catheters having differing stiffness or steering characteristics is often a matter of personal preference of the physician, and some physicians may desire catheters in which the ease of steerability can be altered during the course of a particular procedure. Commercially available catheters, thus, are provided which use different materials in the internal construction in order to provide a variety of characteristics, or the decision to select for use, catheters made by different manufacturers may be based on a comparison of stiffness characteristics of the particular catheters commercially available.

Serious disadvantages result, because the physician must remove and re-insert these different catheters to complete a procedure on a given patient if different steering characteristics are needed during the course of a single procedure.

A need exists for a low cost catheter which could be steered with different degrees of stiffness or resistance to steering forces without removing and re-inserting a different catheter.

SUMMARY OF THE INVENTION

The present invention provides a low cost catheter, usable in both diagnostic and therapeutic applications, that enables a physician to swiftly and accurately change the steering characteristics of the distal end of the catheter as it is steered within the body of a patient. The catheter that embodies the invention allows physicians to better steer a catheter to access various endocardium sites using a single catheter. In its broadest aspect, the invention provides a catheter which enables a physician to alter the physical characteristics of a catheter inserted within a living body by manipulation of external controls.

One aspect of the invention provides a catheter having an internal stiffening member that can be moved within the catheter to either a distally extended or retracted location within the distal tip by external manipulation. Movement of the internal stiffening member results in creating different ease of steering characteristics for bending of the distal tip. The internal stiffening member that the invention provides is usable in connection with unidirectional catheters, as well as bi-directional, steerable catheters.

The invention provides a catheter in which a stiffening member is distally extended within the tip distance to provide greater rigidity and thus stiffer steering characteristics and retracted to a more proximal position to provide the tip with less stiffness and hence easier steering characteristics requiring less steering force. Thus the ease of accessing and measuring electrical activity in all portions of the heart is increased.

An important advantage of the present invention is to provide a catheter which enables the physician to reduce the time required for a procedure by changing the ease of steering obtainable by the catheter while the catheter is still in the patient's body. A yet further aspect of the invention is to provide a catheter steering mechanism wherein a movable stiffening member is provided but wherein currently available steering components and mechanisms can be utilized.

In accordance with a still further aspect of the invention, a movable stiffening member within a catheter is provided by utilizing a stylet that can be proximally-distally manipulated and which is connected to an annular tube, the distal end of which forms a stiffening member within a catheter. A further related aspect is the ability to use such moveable tubes of different materials, having different rigidity characteristics. In this regard, relatively rigid material can be used to provide a greater change in stiffness characteristics upon distal extension of the stiffening member and a more pliable tube could be used, if desired, to produce a lesser degree of change of characteristics. In accordance with still further aspects of the invention, it is possible to substitute a different slidable stiffening mechanism within the catheter, for example, a movable interior stiffening rod can be employed rather than an annular tube.

Briefly summarized, the invention provides a catheter for percutaneous insertion into a living body having a steering mechanism that includes an elongated body bendable in response to external forces to steer the catheter tip. The body has a proximal end for attachment to a guide tube located within the body of the catheter and a distal end for carrying an operative component such as a tip electrode. At least one steering wire is attached to the elongated body for transmitting bending force to the body from a remote control mechanism. An axially movable, bendable, stiffening member, preferably in the form of an axially movable sleeve or rod provides a variable resistance to bending of the body in response to an applied bending force. A control stylet, wire or tube extends through the length of the catheter body and is attached to the stiffening member for moving the stiffening member in a distal/proximal direction.

Further, objects and advantages of the invention will become apparent from the following detailed description and accompanying drawings.

BRIEF DESCRIPTION OF DRAWINGS

FIG. 1 is a top view of a catheter and catheter handle assembly in accordance with the invention with some interior parts shown by means of phantom lines;

FIG. 2 is a view of the catheter shown in FIG. 1 with the tip portion broken away and shown in cross-section on a greatly enlarged scale and showing a moveable sleeve in a proximal position;

FIG. 3 is a view in accordance with FIG. 2 showing the sleeve in a more distal position;

FIG. 4 is a top sectional view of the handle of the device of the present invention on a greatly enlarged scale;

FIG. 5 is a sectional view of a tip portion of a catheter in accordance with another embodiment of the invention;

FIG. 6 is a view of the device of FIG. 5 with the curve adjusting mandrel advanced to a more distal position;

FIG. 7 is a view of a catheter showing an alternate embodiment of the invention utilizing a rotatable sleeve;

FIG. 8 is a perspective view showing the configuration of the distal end of the sleeve of the device shown in FIG. 7;

FIG. 9 is a fragmentary cross-sectional view showing the control mechanism in the distal portion of the handle of the handle of the catheter of FIG. 7;

FIG. 10 is a view of a catheter showing bendable actually movable stiffening member in a retracted approximal position, and;

FIG. 11 is a sectional view of the distal tip portion of the catheter of FIG. 10 with the stiffening member advanced to its most distal position.

DETAILED DESCRIPTION OF PREFERRED EMBODIMENTS

FIG. 1 shows a steerable electrophysiology catheter 10 that embodies the features of the invention. The catheter 10 includes several main parts: a handle 12, a catheter tube or body 14, and a distal steering assembly 16. In use, the catheter 10 provides electrophysiology diagnosis or therapy in the interior regions of the heart.

When used for this purpose, a physician grips the handle 12 and maneuvers the catheter body 14 through a main vein or artery (which is typically the femoral vein) into the interior region of the heart that is to be treated. The physician then further steers the distal tip antenna assembly 16 to place it in contact with the tissue that is to be ablated. The physician directs energy an electrode in the distal tip assembly 16 to ablate the tissue contacted.

As FIG. 4 shows, the handle 12 encloses a steering mechanism which may be in the form of a rotating cam wheel of the type shown in U. S. Pat. No. 5,195,968. While one form of steering mechanism 18 is shown for purposes of illustration, it will be understood that many other mechanisms that allow for selective pulling of the steering wires in the catheter can be substituted.

As FIG. 4 best shows, the handle assembly 12 includes a housing 20 that encloses the steering mechanism 18. The steering mechanism 18 includes a rotatable wheel or cam 22 carried on a shaft 24 within the housing 20. The rotatable cam 22 and control knob 26 are attached to shaft 24 by splines. Clockwise movement of the control knob 26 rotates the cam 22 clockwise pulling on wire 56. Counterclockwise movement of the control knob 26 reverses the direction of each of these movements and results in pulling wire 58. Various other mechanisms can be substituted to apply tension to wires 56 and 58 in place of that shown in FIG. 4.

The steering wires 56 and 58 exit the front of the housing 20 through the interior bore of a tension screw assembly 60. The distal ends of the steering wires 56 and 58 are attached to a steering wire or spring in the electrode tip assembly 16.

The catheter body 14 is a flexible shaft attached to the handle 12. While it can be variously constructed, in a preferred embodiment, the catheter body 14 is a length of stainless steel coiled into a flexible spring 25 enclosing an interior bore 27 which in turn is enclosed in a braided sheath 29 of plastic material. The steering wires 56 and 58 preferably pass through the interior bore 27, which leads to the assembly 16 where the steering wire are attached to a bendable main support wire 34. In the illustrated embodiment, the main support wire 34 is made of stainless steel flat wire stock in an elongated shape about 0.035 inch wide and about 0.005 inch thick. Preferably the main support wire 34 is about 3 inches in total length.

In the distal end of the catheter body 14 there is no surrounding sheath or shield, leaving the steering assembly exposed. Positioned in the distal end region and overlying the distal end of coil 25 is a curve adjusting tube 61. The proximal end of curve adjusting tube 61 is, attached to a mandrel 62 that extends within the catheter body 14 into handle 12. The proximal end of mandrel 62 is connected to a slidable, bi-directional adjuster knob 64. Sliding of knob 64 enables the practitioner to slide the adjusting tube 60 axially within the catheter body 14 to a more proximal or more distal location as desired. The more proximal and more distal positions of knob 64 are shown in FIG. 1 by means of phantom lines. In the more proximal location illustrated in FIG. 2, the curve adjusting tube 61 is positioned to permit the maximum curvature of distal tip assembly 16 to position 16a illustrated by means of phantom lines. In the more distal location illustrated in FIG. 3, the tube 61, which acts as a slidable stiffening member and/or fulcrum for the tip, steering of the tip by means of knob 26 causes a shorter portion of the tip 16 to curve to a sharper curve illustrated by phantom lines 16b in FIG. 3.

In the alternate embodiment illustrated in FIGS. 5 and 6, the mandrel 62, which may be provided with an enlarged end section, is positioned for axial sliding within a channel 66 in similar to that shown in FIGS. 2 and 3 the distal tip 16 can be bent to different curvatures 16a or 16b as shown in FIGS. 5 and 6. It will readily be apparent that intermediate curve shapes other than those illustrated by lines 16a and 16b can be provided by positioning level 64 in an intermediate position.

In the preferred embodiment of the device shown in FIGS. 2 and 3 outer sleeve 29 is formed of Kevlar. Mandrel 62 is formed of a 0.02 inch stainless steel wire running parallel between the guide coil 25 and the inside of Kevlar tubing 29. Wire 64 is preferably attached on the outside of a 2.5 inch long 0.050 inch inter diameter/0.055 inch outer diameter length of tube that forms sleeve 60. The tube can be made of stainless steel, nitinol alloy or a polymeric material such as polyamide or other polymer. In the preferred embodiment, a polyamide tube is reinforced by a stainless steel coil embedded in the wall. It will also be apparent that in the event the tube 61 is made from a relatively softer material, it will have less effect on the increase in rigidity of the tip.

In an embodiment shown in FIGS. 7–9 a device is usable in connection with a related invention. A tube 160 is rotatable relative to the steering wire 34 rather than being axially movable relative thereto. In this case a rotatable sleeve concentric with spring 25 and located within bore 27 is attached to tube 160 for the purpose of applying rotational forces thereto. Tube 160 is provided with a distal end having circumferential segments 162, 164, 166, and 168 of differing lengths. Each of these circumferential segments provides a fulcrum or stiffening member spaced a different distance from the distal tip of the catheter and thus provides for as many different curvature shapes of the tip as there are segments.

Tube 160 is rotated by applying a force to control knob 170 located in handle 12. Tube 160 is connected to control handle 170 by means of a torque transmitting tube 172. Since the control wire 34 will tend to bend the distal tip 16 from side to side in a single plane, the fulcrum length provided by rotatable tube 160 is dependent on which of the segments 162, 164, 166 or 168 is positioned in the plane in which control wire 34 bends. Appropriate markings on handle 12 can be provided to indicate the position in which control knob 170 is rotated. Thus, the physician can readily change the fulcrum length or stiffness characteristics of the distal tip of the catheter by manually rotating knob 170.

In the embodiment of FIG. 10, stiffening member 180 is shown in the form of a flexible polymeric tube. Any flexible material can be used as a material of construction for tube 180. A rod 62 of the type in FIGS. 5 and 6 is used as a stiffening member. Any flexible materials such as plastic, metal or other bendable materials of construction can be used.

Referring to FIGS. 10 and 11, when sleeve 180 is in the retracted position shown in FIG. 10, the tip 16 can be steered easily with greatly reduced resistance to bending when bending forces are applied to the tip by means of steering mechanism 18. When the stiffening member 180 is advanced to its most distal position shown in FIG. 11, the same catheter can behave as one that is stiffer or resistant to bending.

It will, thus, be appreciated that in accordance with the invention, the characteristics of the distal tip of a steerable catheter can be altered by means of movement of a remote control member. This alteration can occur when the catheter is being used within a living body. The invention, thus, makes possible the alteration of numerous characteristics of a catheter without the need for withdrawing the catheter from the body.

What is claimed is:

1. A catheter having an electrode tip assembly including
   a body bendable in response to external forces, the body having opposite proximal and distal end portions and being connected to a steering mechanism by at least one steering wire for applying a bending force to the body,
   an external control,
   a stiffening member positioned in the catheter movable relative to said body in response to movement of said external control, said stiffening member being distally extendable and proximally retractable by external manipulation of said external control for varying the stiffness of the body in response to an applied bending force, said catheter being deflectable along the axial length of said tip assembly and having a first resistance to steering forces when said stiffening member is retracted and a second resistance to steering forces greater than said first resistance when said stiffening member is distally extended,
   means located within the catheter for translating a force applied to said external control to said stiffening member for causing the stiffening member to be moved in response to said force,
   said steering mechanism including externally controllable steering means independent of said stiffening member attached to said body for applying a bending force to the body and,
   at least one electrode carried by said tip assembly.

2. A tip assembly according to claim 1 wherein the stiffening member comprises a flexible annular solid sleeve.

3. A tip assembly according to claim 2 wherein the stiffening member comprises a polymeric material.

4. An assembly according to claim 1 wherein said stiffening member is axially movable from a first, distally extended position to a second, retracted position.

5. A catheter including
   an elongated flexible tubular catheter body,
   an electrode tip assembly affixed to the distal end of said catheter body,
   a steering assembly located within the catheter body and connected to said tip assembly including a guide tube and a support wire bendable in response to external forces, the support wire having a proximal end attached to the guide tube distal end and a distal end that extends beyond the guide tube distal end,
   an axially movable stiffening member within said catheter body movable from a first, distally extended position to a second, position retracted from the distal end of the support wire for varying the stiffness of the steering assembly in response to an applied bending force, and
   means attached to said wire for applying a bending force to the wire.

6. A catheter according to claim 5 wherein the stiffening member is in the form of an annular sleeve positioned around the support wire and guide tube.

7. A catheter according to claim 6 comprising a stylet having a proximal end and a distal end and being axially movable within said catheter body, the stiffening member being attached to the distal end of said stylet.

8. An electrode tip assembly for the distal end of a catheter for supporting a tip electrode for percutaneous insertion into a living body comprising
   an elongated body bendable in response to external forces to steer the tip electrode, the body having a proximal end for attachment to the catheter and a distal end for carrying the tip electrode and at least one steering wire attached to the body for transmitting bending force to the body,
   a remote control mechanism connected to said steering wire for application of forces thereto,
   an axially movable flexible stiffening member independent of said remote control mechanism providing a variable resistance to bending of the body in response to an applied bending force,
   a control stylet extending through the length of the catheter body and attached to the stiffening member for moving the stiffening member in a distal/proximal direction
   said catheter being deflectable along the axial length of said tip assembly and having a first resistance to bending forces when said stiffening member is retracted and a second resistance to steering forces greater than said first resistance when said stiffening member is distally extended, and
   at least one electrode carried by said tip assembly.

9. An electrode support assembly according to claim 8 wherein the stiffening member comprises a stiff annularly shaped polymeric tube.

10. A cardiac probe including an elongated, flexible tubular catheter body,
    a distal tip assembly, bendable along its axial length including at least one electrode for measurement of electrical activity within the heart or for ablation of cardiac tissue,
    said probe including a handle portion provided with a steering mechanism and at least one steering wire connected to said steering mechanism and extending from said handle to said distal tip assembly for bending said assembly in response to forces applied to said steering mechanism, an elongated body bendable in response to external forces to steer the tip electrode, the body having a proximal end for attachment to the catheter and a distal end for carrying the tip electrode, said at least one steering wire being attached to the body for transmitting bending force to the body, characterized in that a stiffening member is contained in said catheter body adjacent to said distal tip assembly, said stiffening member being operatively connected to and manipulatable by a manually moveable control, independent from said steering mechanism and steering wire, located in said handle and wherein manipulation of said control moves said stiffening member axially relative to said steering mechanism from a retracted position wherein said distal tip assembly has a first resistance to bending to an extended position wherein said distal tip assembly has a second resistance to bending greater than said first resistance to bending, when said distal tip assembly is caused to bend to said force, and, steering means attached to said body for applying a bending force to the body.

11. A catheter including an elongated flexible tubular catheter body having a proximal end and a distal end, said distal end supporting a steerable distal tip assembly which includes a distal tip, and said proximal end being connected to a handle, said handle containing a mechanism operatively connected to said distal tip assembly for steering and bending said distal tip, said catheter being provided with an internal means within said distal tip assembly for altering the physical stiffness characteristics of the distal tip independently of said steering mechanism, said means being operatively connected to a control located in said handle for effecting said alteration from a first stiffness characteristic to a second stiffness characteristic different from said first stiffness characteristic, said mechanism being operative to effect bending of said distal tip when it is deployed with either of said first and second characteristics.

* * * * *